(12) United States Patent
Makino

(10) Patent No.: US 10,718,776 B2
(45) Date of Patent: Jul. 21, 2020

(54) METHOD FOR DETECTING BIOLOGICAL SUBSTANCE

(71) Applicant: TOPPAN PRINTING CO., LTD., Taito-ku (JP)

(72) Inventor: Yoichi Makino, Taito-ku (JP)

(73) Assignee: TOPPAN PRINTING CO., LTD., Taito-ku (JP)

( * ) Notice: Subject to any disclaimer, the term of this patent is extended or adjusted under 35 U.S.C. 154(b) by 0 days.

(21) Appl. No.: 15/914,756

(22) Filed: Mar. 7, 2018

(65) Prior Publication Data

US 2018/0196059 A1 Jul. 12, 2018

Related U.S. Application Data

(63) Continuation of application No. PCT/JP2016/076302, filed on Sep. 7, 2016.

(30) Foreign Application Priority Data

Sep. 8, 2015 (JP) ................. 2015-176868

(51) Int. Cl.
*G01N 33/58* (2006.01)
*C12Q 1/68* (2018.01)
(Continued)

(52) U.S. Cl.
CPC ............... *G01N 33/58* (2013.01); *C12Q 1/68* (2013.01); *C12Q 1/686* (2013.01); *G01N 33/6803* (2013.01)

(58) Field of Classification Search
CPC .... G01N 33/58; G01N 33/6803; C12Q 1/686; C12Q 1/68
See application file for complete search history.

(56) References Cited

U.S. PATENT DOCUMENTS

| 5,183,744 A | 2/1993 | Kawamura et al. |
| 6,440,706 B1 | 8/2002 | Vogelstein et al. |

(Continued)

FOREIGN PATENT DOCUMENTS

| JP | 2011-211946 A | 10/2011 |
| JP | 4911592 B2 | 4/2012 |

(Continued)

OTHER PUBLICATIONS

"Hologic" Retrieved on Dec. 3, 2019 from the internet: https://www.hologic.com/sites/default/files/package-insert/15-2465_101_01.pdf (Year: 2015).*

(Continued)

*Primary Examiner* — Joseph G. Dauner
(74) *Attorney, Agent, or Firm* — Oblon, McClelland, Maier & Neustadt, L.L.P.

(57) ABSTRACT

A method of detecting a biological substance, including introducing a first substance dispersed in a solvent into a flow channel formed between a first substrate and a second substrate such that the first substance is placed in a first well formed in the first substrate, and detecting the first substance. The first well is formed such that the first well has an open side which faces downwards and is communicated with the flow channel, and the solvent has a specific gravity larger than a specific gravity of the first substance.

20 Claims, 11 Drawing Sheets

OBSERVATION DIRECTION

(51) Int. Cl.
  *C12Q 1/686* (2018.01)
  *G01N 33/68* (2006.01)

(56) References Cited

U.S. PATENT DOCUMENTS

| | | | |
|---|---|---|---|
| 6,753,147 | B2 | 6/2004 | Vogelstein et al. |
| 7,824,889 | B2 | 11/2010 | Vogelstein et al. |
| 7,915,015 | B2 | 3/2011 | Vogelstein et al. |
| 8,859,206 | B2 | 10/2014 | Vogelstein et al. |
| 9,180,453 | B2 * | 11/2015 | Chiu .................. B01L 3/502784 |
| 9,329,174 | B2 | 5/2016 | Noji et al. |
| 2005/0130176 | A1 | 6/2005 | Vogelstein et al. |
| 2009/0111141 | A1 * | 4/2009 | Deutsch ............... B01J 19/0046 435/30 |
| 2010/0041046 | A1 * | 2/2010 | Chiu .................. B01L 3/502784 435/287.2 |
| 2010/0216193 | A1 * | 8/2010 | Gomi ................... B01L 3/5025 435/91.2 |
| 2010/0311616 | A1 * | 12/2010 | Ozawa .................. B01L 3/5025 506/39 |
| 2015/0038341 | A1 | 2/2015 | Vogelstein et al. |
| 2015/0087547 | A1 | 3/2015 | Noji et al. |
| 2015/0165346 | A1 * | 6/2015 | Puleo ................. B01D 21/0087 210/695 |
| 2016/0096172 | A1 * | 4/2016 | Chiu ................. B01L 3/502784 435/309.1 |
| 2016/0223531 | A1 | 8/2016 | Noji et al. |
| 2016/0333400 | A1 * | 11/2016 | Makino ................. C12Q 1/6858 |
| 2017/0115284 | A1 | 4/2017 | Noji et al. |
| 2017/0176430 | A1 | 6/2017 | Noji et al. |
| 2018/0221877 | A1 * | 8/2018 | Goto ...................... G01N 21/03 |
| 2019/0217289 | A1 * | 7/2019 | Chiu ....................... B01L 3/502 |

FOREIGN PATENT DOCUMENTS

| | | | |
|---|---|---|---|
| WO | WO 2009/054473 A1 | 4/2009 | |
| WO | WO 2013/187382 A1 | 12/2013 | |
| WO | WO-2014210207 A1 * | 12/2014 | .......... B01L 3/50851 |

OTHER PUBLICATIONS

International Search Report dated Dec. 13, 2016 in PCT/JP2016/076302, filed Sep. 7, 2016, citing documents AO, AP, AQ and AR therein, 5 pages.

Dube et al., "Mathematical Analysis of Copy Number Variation in a DNA Sample Using Digital PCR on a Nanofluidic Device", PLOS One, Aug. 2008, vol. 3, Issue 8, e2876, pp. 1-9.

Kim et al., "Large-scale femtoliter droplet array for digital counting of single biomolecules", Lab on a Chip, 2012, 12, 4986-4991.

* cited by examiner

OBSERVATION DIRECTION

OBSERVATION DIRECTION

OBSERVATION DIRECTION

OBSERVATION DIRECTION

METHOD FOR DETECTING BIOLOGICAL SUBSTANCE

CROSS-REFERENCE TO RELATED APPLICATIONS

The present application is a continuation of International Application No. PCT/JP2016/076302, filed Sep. 7, 2016, which is based upon and claims the benefits of priority to Japanese Application No. 2015-176868, filed Sep. 8, 2015. The entire contents of these applications are incorporated herein by reference.

BACKGROUND OF THE INVENTION

Field of the Invention

The present invention relates to a method for detecting biological substance.

Discussion of the Background

Patent Literature (PTL) 1 to 3 and Non-patent Literature (Non-PTL) 1 and 2, for example, describe technology related to a method for detecting biological substance.
PTL 1 JP 2003-511009 A
PTL 2 JP 4,911,592 B
PTL 3 JP 5,337,324 B
Non-PTL 1 "Mathematical Analysis of Copy Number Variation in a DNA Sample Using Digital PCR on a Nanofluidic Device", PLOS ONE, August 2008, Volume 3, Issue 8, e 2876, p 1-p 9
Non-PTL 2 "Lab on a Chip", 2012, DOI: 10.1039/c21x40632b

SUMMARY OF THE INVENTION

According to an aspect of the present invention, a method of detecting a biological substance includes introducing a first substance dispersed in a solvent into a flow channel formed between a first substrate and a second substrate such that the first substance is placed in a first well formed in the first substrate, and detecting the first substance. The first well is formed such that the first well has an open side which faces downwards and is communicated with the flow channel, and the solvent has a specific gravity larger than a specific gravity of the first substance.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE EMBODIMENTS

Figure 1:
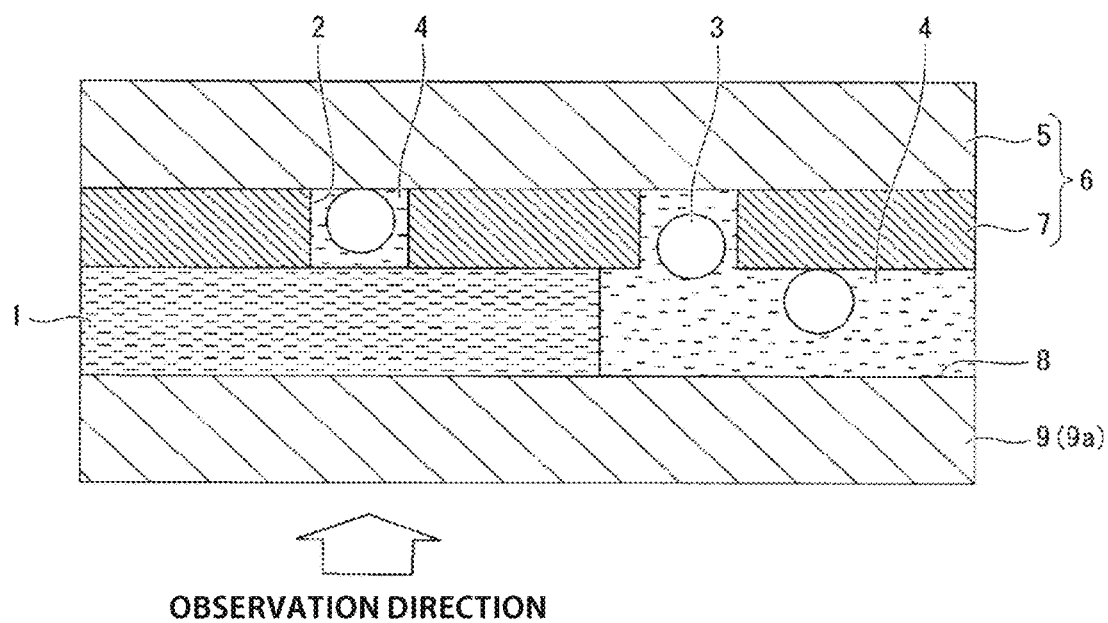
FIG. 1 illustrates in cross-section the configuration of a biomolecule analysis kit employing a method for detecting biological substance according to a first embodiment of the present invention.

Embodiments of the present invention will be described with reference to the accompanying drawings.

The drawings are schematic, and thus the relationships between thicknesses and planar dimensions, the ratios of the thicknesses of each of the layers, and the like are different from the actual case. For simplification of the drawings, known structures are simply illustrated. Moreover, like reference characters are used for components displaying the same or similar function in each of the drawings, with duplicate description of these components omitted. The embodiments described below illustrate an example configuration for embodying the technical idea of the present invention, and thus the material, shape, structure and the like of the components of the present invention are not limited to those described in the following. Various modifications can be made to the technical idea of the present invention within the technical range defined by the claims.

First Embodiment

FIG. 1 illustrates in cross-section the configuration of a biomolecule analysis kit employing a method for detecting biological substance according to a first embodiment of the present invention. FIG. 1 illustrates in longitudinal cross-section a part of the biomolecule analysis kit. The biomolecule analysis kit includes an array device (not illustrated). This array device is formed by aligning a plurality of microwells 2 (described later) in the vertical and horizontal directions. By introducing a hydrophilic solvent 4 or an oily sealant 1 described later to the array device, a biomolecule analysis kit with microbeads (first matter, beads) contained in the microwells (first wells) 2 is formed. In each of the subsequent figures, the direction of gravity (vertical direction) indicates the direction from a substrate portion 6 side described later toward a cover portion 9 side.

In the biomolecule analysis kit of FIG. 1, a biomolecule such as DNA, RNA, miRNA, mRNA, or protein is selected as the biomolecule to be analyzed.

As illustrated in FIG. 1, the biomolecule analysis kit includes a substrate portion (first substrate) 6 that has a microporous-array layer 7 in which a plurality of microwells 2 as reaction vessels are aligned in an array, and a cover portion (second substrate) 9, with a flow channel 8 formed between the substrate portion 6 and the cover portion 9 (9a). Here, in the present invention, "down" means "the direction of gravity (vertical direction)" and "up" means "the direction opposite the direction of gravity (vertical direction)".

The substrate portion 6 includes a glass substrate 5 and a microporous-array layer 7 laminated on the glass substrate 5 as a reaction field.

The microwells 2 formed in the microporous-array layer 7 are, for example, spaces with a bottomed cylindrical shape having a diameter of 5 µm, a depth of 5 µm and an open portion on one end. In the microporous-array layer 7, an array of a plurality of microwells 2 is formed. In other words, the microwells 2 are vertically and horizontally aligned in an array in the microporous-array layer 7.

For example, the microwells 2 are arranged in a grid along each side with respect to a surface having a rectangular shape that is 5 mm in length and width. The spacing between the microwells 2 is set according to a resolution that is capable of independently detecting a signal in each microwell 2.

The volume of a microwell 2 may be appropriately set; however, the smaller the volume of the microwell 2, the more the reaction time until signal detection is possible can be shortened. As an example, the volume of a microwell 2 is 100 picoliters or less.

The microporous-array layer 7 and the glass substrate 5 may be the same material, and may be integrally formed using a mold or the like. Alternatively, microporous-array layer 7 formed of resin or the like by photolithography may be formed on the glass substrate 5. Still alternatively, a microporous-array layer 7 having microwells 2 may be formed on a member separate from the glass substrate 5, and by fixing this member to the glass substrate 5 with adhesive or the like, the microporous-array layer may be provided on one surface of the glass substrate 5.

The cover portion 9a is disposed on the surface of the substrate portion 6 where the microporous-array layer 7 is formed, and with a space between the cover portion 9a and the substrate portion 6, faces the substrate portion 6 so as to face the open portions of the microporous-array layer 7, that is, the open portions of the microwells 2. More specifically, the cover portion 9a is arranged so that the substrate portion 6 is disposed above the cover portion 9a with a space therebetween. The space between the substrate portion 6 and the cover portion 9a serves as the flow channel 8 through which various fluids flow for detecting a target or the like.

The cover portion 9a needs to be observable in the observation direction illustrated in FIG. 1, or, in other words, in a direction toward the microwells 2 from the surface on the opposite side of the cover portion 9a from the flow channel 8. Thus the cover portion 9a preferably is transparent. Transparency in this case includes the transmission of wavelengths that will be observed (excitation light, fluorescent light, and the like).

The material of the microwells 2, that is, the material of the microporous-array layer 7 forming the inner wall of the microwells 2, may be resin, glass or the like. The material of the microwells 2 may be the same as or different from the material of the substrate portion 6. Moreover, the microwells 2 may be integrated with the same material as the substrate portion, or may be integrally formed with the same material as the substrate portion 6.

Examples of the material of the microporous-array layer 7 forming the substrate portion 6 of resin include cyclo-olefin polymer, silicon, polypropylene, polycarbonate, polystyrene, polyethylene, polyvinyl acetate, fluororesin, amorphous fluororesin, and CYTOP (registered trademark).

These example materials of the microwells 2 are merely illustrative, and do not limit the material of the microwells 2.

In the biomolecule analysis kit according to this embodiment, at least a part of the microwells 2 preferably is hydrophobic. In other words, at least part of the microwells 2 has a portion having hydrophobicity. Here, hydrophobicity means that when the contact angles of hydrophilic solvent 4 and oily sealant 1 are measured on the surface of a portion (material) having hydrophobicity, the contact angle of the oily sealant 1 is smaller than the contact angle of the hydrophilic solvent 4. The contact angle can be measured with typical measurement equipment.

The thickness of the glass substrate 5 is appropriately set so that when a plurality of microwells 2 are formed using an imprinting method, for example, the glass substrate 5 has sufficient strength as a substrate in the process of forming the microwells 2.

The volume of the microwells 2 can be appropriately set. For example, for shorter time required to saturate a signal and to generate a sufficient signal, the volume of the microwells 2 is set based on the amount of liquid at which the number of molecules to be analyzed becomes one or less per well.

The hydrophilic solvent 4 of this embodiment is a solution containing at least one of a sample that contains the target substance to be analyzed, and a detection reaction reagent described above (Invader reaction reagent or PCR reaction reagent). This hydrophilic solvent 4 may also contain an adsorption inhibitor (described later) as necessary.

The hydrophilic solvent 4 is sent from an inlet portion (not illustrated) to the space formed between the substrate portion 6 and the cover portion 9a, or, in other words, the flow channel 8.

The hydrophilic solvent 4 for dispersing the microbeads 3 has a larger specific gravity than the microbeads 3, does not mix with the oily sealant 1 described later, and is hydrophilic or hydrophobic. Preferably, the hydrophilic solvent 4 is transparent. More preferably, a reagent may be mixed with the hydrophilic solvent 4 for detecting biomolecules captured by the microbeads 3 so that biomolecules can be detected after droplets are formed in the microwells 2.

The material of the microbeads 3 is not limited as long as the microbeads 3 have a smaller specific gravity than the hydrophilic solvent 4, and have a size capable of fitting inside the microwells 2. Preferably, the microbeads 3 are labeled for capturing biomolecules; for example, an antibody or the like is selected to capture protein.

Moreover, not only artificial microbeads, but also particles of cellular or biological origin can be used.

As an example of microbeads 3, magnetic beads can be used. Magnetic beads are magnetic polymer particles containing a magnetic substance and a polymer layer that covers the magnetic substance. A magnetic polymer particle may be present as one polymer particle covered by a plurality of magnetic substances. As the substance coating the polymer particles, ferrite particles such as magnetite or the like that is capable of generating minute particles in water are preferable. As a substance other than ferrite, minute particles of various magnetic metals or various magnetic compounds, for example, can be used, and the respective characteristic magnetic properties of these substances can be utilized in various ways. The target substance to be analyzed is then captured by the microbeads 3. The capture method is an antigen-antibody reaction that uses antibody-modified microbeads when the target substance to be analyzed is an antigen protein. When the target substance to be analyzed is DNA, the capture is performed by hybridization using probe-modified microbeads.

As another example of microbeads, polymer beads can be used. Polymer beads have a smaller specific gravity than magnetic beads, so they can be distributed more efficiently into the microwells.

The specific gravity of the hydrophilic solvent is not limited as long as it is larger than that of the microbeads. The larger the difference in specific gravity with that of the microbeads is, the easier it is to obtain the effect. A method for increasing the specific gravity may be, for example, to dissolve a water-soluble substance in the hydrophilic solvent. As a water-soluble substance to be dissolved in the hydrophilic solvent, a substance such as a sugar or the like that does not inhibit the enzymatic reaction can be selected when an enzymatic reaction or the like is performed in the microwells. For example, when sucrose is saturated in water, the specific gravity can be set to 1.3. As another example, a reagent such as Percoll (manufactured by GE Healthcare) or the like that creates a density gradient may be used.

The oily sealant 1 is a solution that can be sent from an inlet portion (not illustrated) to the space formed between the substrate portion 6 and the cover portion 9a, or, in other words, the flow channel 8. The oily sealant 1 is a solution that can be sent from an inlet portion (not illustrated) to the space formed between the substrate portion 6 and the cover portion 9a, or, in other words, the flow channel 8. Mineral oil may also be used as the oily sealant 1. The oily sealant 1 is introduced into the flow channel 8 after the hydrophilic solvent 4 is introduced into the flow channel 8.

Here, microbeads 3 are dispersed in the hydrophilic solvent 4, and the hydrophilic solvent 4 has a larger specific gravity than the microbeads 3. In other words, the microbeads 3 in the hydrophilic solvent 4 will float.

Therefore, when hydrophilic solvent 4 is introduced into the flow channel 8, microbeads 3 are positioned above the flow channel 8, with the microwells 2 arranged on the upper surface of the flow channel 8 and open to the flow channel 8 side. Therefore, a microbead 3 floating in the hydrophilic solvent 4 becomes located in a microwell 2 after the microbead 3 reaches a position facing the microwell 2.

After the hydrophilic solvent 4 is introduced into the flow channel 8, the oily sealant 1 is introduced into the flow channel 8. This causes a surplus portion of the hydrophilic solvent 4, that is, the portion not contained inside the microwells 2, to be displaced by the oily sealant 1, so that the flow channel 8 becomes filled with the oily sealant 1. As a result, a biomolecule analysis kit is obtained in which the microbeads 3 are contained inside the microwells 2 and the flow channel 8 is filled with oily sealant 1.

Therefore, for example, a signal amplification reaction reagent is contained in the hydrophilic solvent 4 beforehand, a signal amplification reaction is performed inside the microwells 2, and signal detection of the microbeads 3 contained inside each of the microwells 2 is performed. This configuration facilitates, for example, density detection and the like.

In a biomolecule analysis kit obtained in this way, the microbeads 3 do not come in contact with the bottom surface of the flow channel 8, that is, the cover portion 9a side. Therefore, when observing from the cover portion 9a side as the observation direction, the light-emitting state of the microbeads 3 in the entire area on the cover portion 9a side can be observed. Therefore, compared with the method of distributing the microbeads into wells formed on the bottom surface side of the flow channel, the light-emitting state can be detected with higher accuracy, that is, density detection and the like can be performed with better accuracy.

The signal amplification may be an isothermal reaction, the isothermal reaction may be an enzymatic reaction. The enzymatic reaction may be an Invader reaction.

The signal detection may be performed by detecting any one or more of fluorescence, light emission, pH change, absorbance change, potential change, and electric current change that correspond to the presence/absence of a biological substance inside the microwells 2.

Together with containing any of DNA, RNA, miRNA, mRNA and protein as the target substance to be analyzed, the hydrophilic solvent 4 may also contain a template nucleic acid as a labeling substance having a specific labeling ability for the target substance to be analyzed, or may also contain the labeling substance in the solvent in a bondable state.

Together with containing any of DNA, RNA, miRNA, mRNA and protein as the target substance to be analyzed, the hydrophilic solvent 4 may also contain a template nucleic acid as a labeling substance having a specific labeling ability for the target substance to be analyzed, or may also contain the labeling substance in the solvent in a bondable state.

Variation of the First Embodiment

Although a glass substrate 5 is used in this embodiment, the present invention is not limited to this. For example, instead of a glass substrate 5, a substrate formed of a transparent polymeric material may be used.

First Examples

The effect of the present invention will be described in detail using the following examples. The present invention is not limited to these examples.

Example 1

<Preparation of an Array Device>

CYTOP (registered trademark) was spin coated on a 0.5 mm thick glass substrate 5 and allowed to thermally cure for three hours at 180° C. Then a substrate portion 6 having 1 million pores each with a diameter of 5 µm was prepared by photolithography. A microporous-array layer 7 was formed by performing photolithography molding of the layer formed by spin coating CYTOP on the glass substrate 5. The thickness of the layer formed by spin coating CYTOP on the glass substrate 5, that is, the thickness of the microporous-array layer 7, is 3 μm.

Then, a cover glass was set as a cover portion 9a so that the space between the cover portion 9a and the substrate portion 6 was 100 μm. A spacer made of an adhesive tape was placed between the substrate portion 6 and the cover portion 9a, and a flow channel 8 was formed. A solvent was fed as a substitute liquid between the substrate portion 6 and the cover portion 9a, and the solvent was filled into the 5 μm diameter pores, and into the entire space between the substrate portion 6 and the cover portion 9a. In this example, the composition of the solvent is 20 μM MOPS pH 7.5, 15 mM NaCl, and 6.25 mM $MgCl_2$.

<Supplying a Solution of Beads>

The array device was placed so that the microwells 2 were located above the flow channel 8. Microbeads (fluorescent microbeads) 3 having a diameter of 3 μm were mixed with the hydrophilic solvent 4 and fed into the flow channel 8. Then, FC-40 (manufactured by Sigma) was fed into the flow channel 8 as an oily sealant 1, and the microbeads 3 were distributed into the microwells 2. In this example, the composition of the solvent is 20 μM MOPS pH 7.5, 15 mM NaCl, and 6.25 mM $MgCl_2$. To make the specific gravity of the hydrophilic solvent 4 larger than that of the microbeads 3, the specific gravity of the hydrophilic solvent 4 was adjusted by adding Percoll (manufactured by GE Healthcare).

<Measurement of the Encapsulated Microbeads>

The number of microbeads 3 contained in the microwells 2 was observed with a fluorescence microscope. Here, the microbeads 3 were observed using a fluorescence microscope (manufactured by Olympus), a light source (FluoArc 001.26A Usable with HBO 10, manufactured by LEJ), a sensor (manufactured by Hamamatsu Photonics), a fluorescent filter, and analysis software (MetaMorph, manufactured by Molecular Devices). In the case of microbeads 3 having a 3 μm diameter, bright field observation using transmitted light is also possible, so observation in a bright field was also performed.

Comparison Example 1

Except for the specific gravity of the hydrophilic solvent 4 being smaller than that of the microbeads 3, the encapsulated microbeads 3 were observed with a microscope in the same way as in Example 1.

(Observation Results)

Figure 2A:
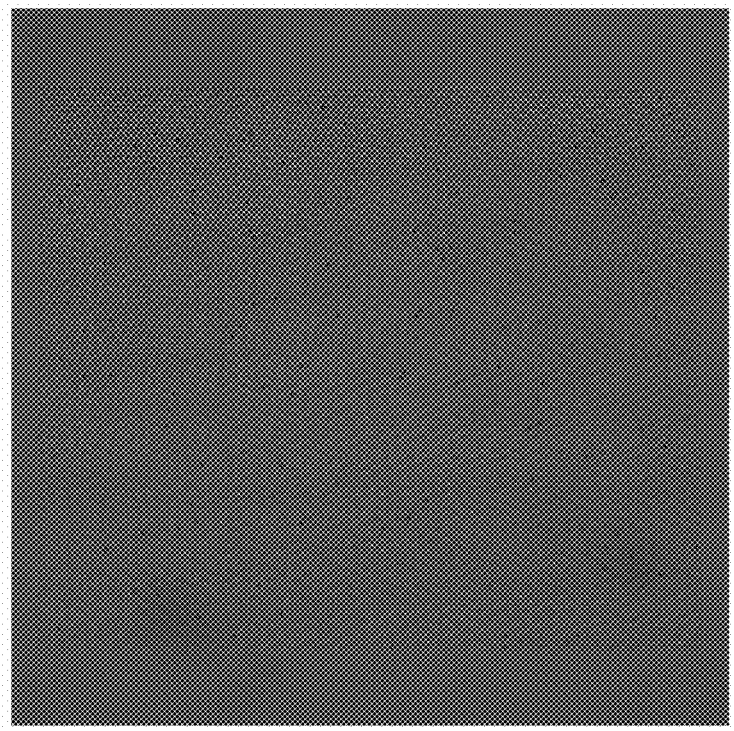
FIG. 2A is a photograph illustrating the result of observation of an array device and microbeads in Example 1 using transmitted light microscopy.
Figure 2B:
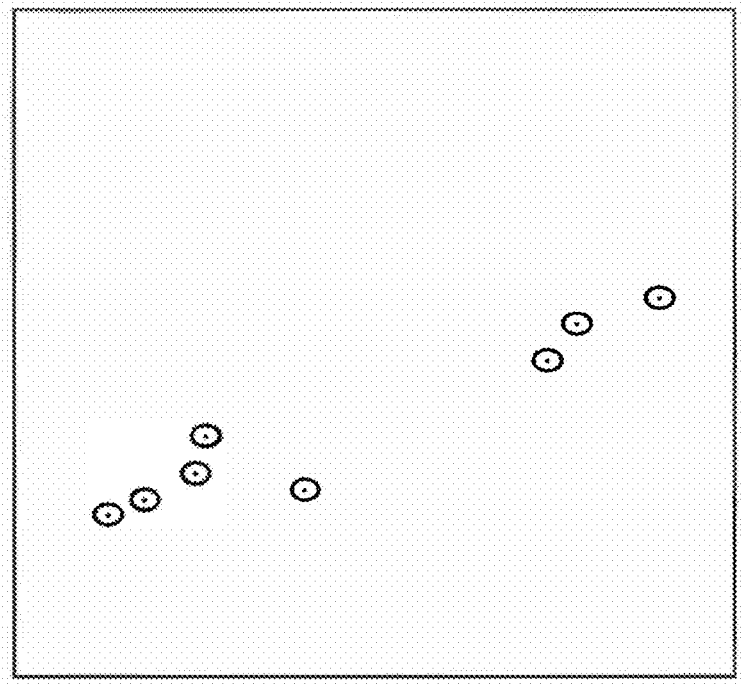
FIG. 2B is an explanative diagram illustrating the result of observation of the array device and microbeads in Example 1 using transmitted light microscopy.

FIG. 2A is a photograph illustrating the result in Example 1 of observing the array device in which the microbeads 3 are contained in the microwells 2 using transmitted light microscopy. FIG. 2B is an explanative diagram illustrating the result in Example 1 of observing the array device in which the microbeads 3 are contained in the microwells 2 using transmitted light microscopy. FIG. 2B illustrates the main part of FIG. 2A. FIG. 2A and FIG. 2B are illustrated on the same scale. In the following, FIG. 2A and FIG. 2B are collectively referred to as "FIG. 2".

Figure 3:
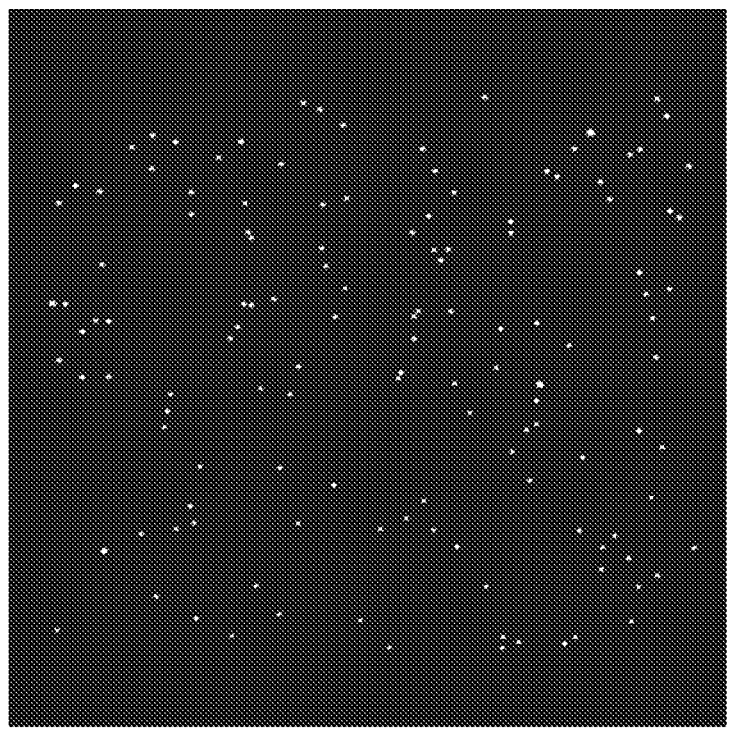
FIG. 3 is a photograph illustrating the result of fluorescence observation of the array device and microbeads in Example 1 using a microscope.

FIG. 3 is a photograph illustrating the results in Example 1 of fluorescence observation of the array device in which the microbeads 3 are contained in the microwells 2 using a microscope.

Figure 4A:
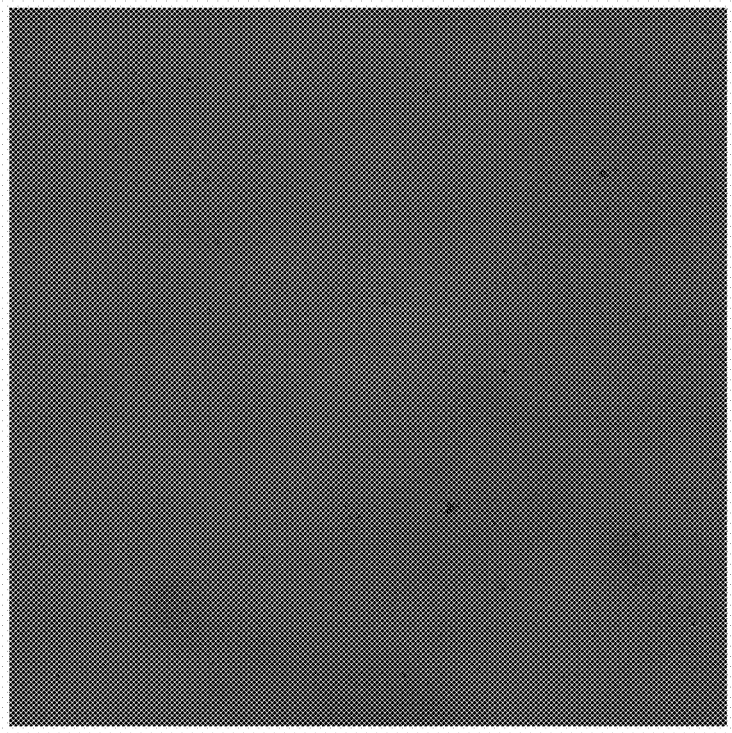
FIG. 4A is a photograph illustrating the result of observation of an array device and microbeads in Comparative Example 1 using transmitted light microscopy.
Figure 4B:
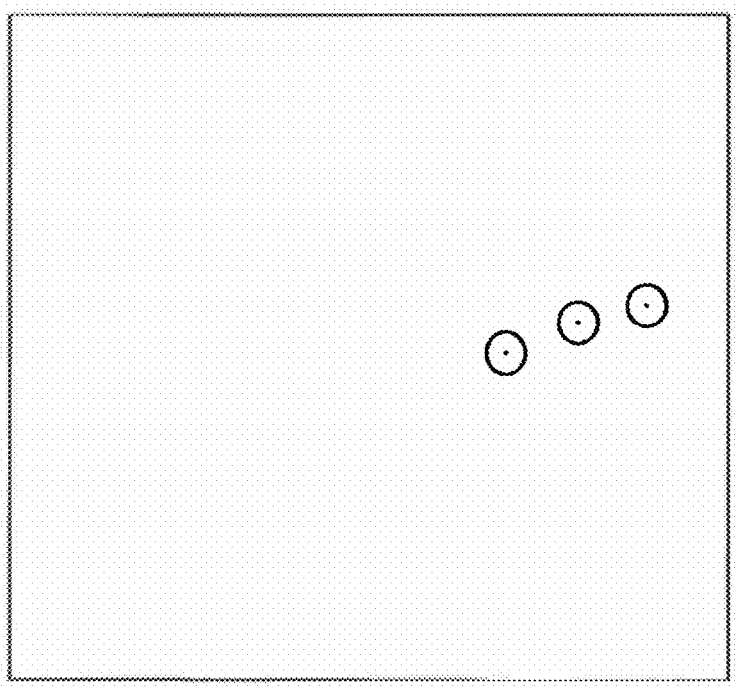
FIG. 4B is an explanative diagram illustrating the result of observation of the array device and microbeads in Comparative Example 1 using transmitted light microscopy.

FIG. 4A is a photograph illustrating the results in Comparative Example 1 of observing the array device in which the microbeads 3 are contained in the microwells 2 using transmitted light microscopy. FIG. 4B is an explanative diagram illustrating the result in Comparative Example 1 of observing the array device in which the microbeads 3 are contained in the microwells 2 using transmitted light microscopy. FIG. 4B illustrates the main part of FIG. 4A. FIG. 4A and FIG. 4B are illustrated on the same scale. In the following, FIG. 4A and FIG. 4B are collectively referred to as "FIG. 4".

Figure 5:
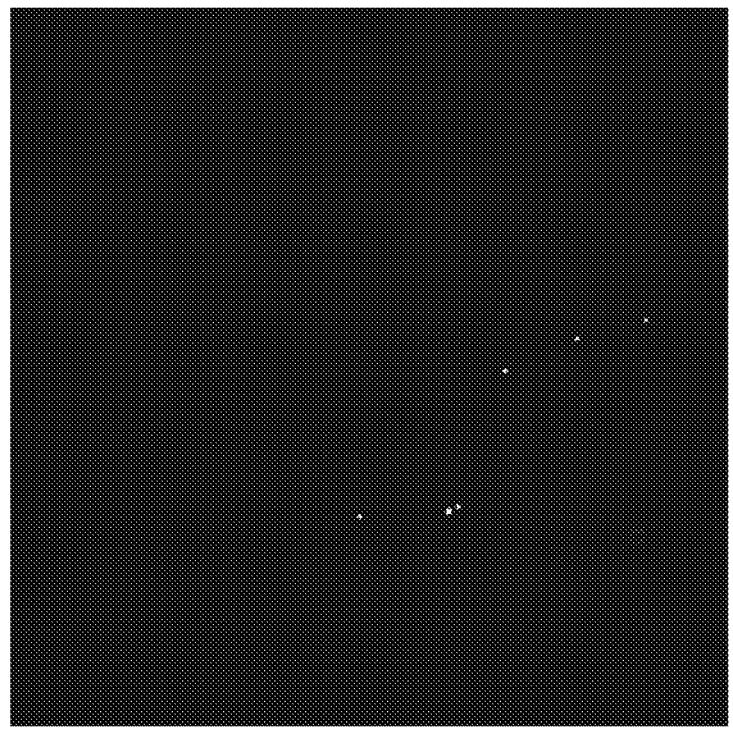
FIG. 5 is a photograph illustrating the result of fluorescence observation of the array device and microbeads in Comparative Example 1 using a microscope.

FIG. 5 is a photograph illustrating the results in Comparative Example 1 of fluorescence observation of the array device in which the microbeads 3 are contained in the microwells 2 using a microscope.

In the observation results of FIG. 2 and FIG. 4 using transmitted light microscopy, the black dots in the array device represent microwells 2 in which transmitted light was detected, or, in other words, microwells 2 that do not contain microbeads 3. That is, the number of microwells 2 in which no microbeads 3 are contained is less in Example 1 than in Comparative Example 1, or, in other words, it can be seen that more microbeads 3 are contained. FIG. 2 and FIG. 4 show black dots representing microbeads, some of which are circled. Overall, FIG. 2 contains more black dots than FIG. 4.

In the results of FIG. 3 and FIG. 5 of fluorescence observation using a microscope, the white dots in the array device represent fluorescence emission by the microbeads, or, in other words, microwells 2 that contain microbeads 3. That is, the number of microwells 2 in which microbeads 3 are contained is more in Example 1 than in Comparative Example 1, or, in other words, it can be seen that more microbeads 3 are contained.

From these results, it was confirmed that in Example 1 in which the specific gravity of the hydrophilic solvent 4 is larger than that of the microbeads 3, the efficiency of encapsulating microbeads 3 in the microwells 2 is higher.

In the following examples, the specific gravities of the hydrophilic solvent 4 and the microbeads 3 were more finely adjusted than in Example 1 and Comparative Example 1 described above. By doing so, the efficiency of encapsulating the microbeads 3 in the microwells 2 was examined in more detail.

Example 2

Except for the specific gravity of the hydrophilic solvent 4 being set to 1.09 and the specific gravity of the microbeads 3 being set to 1.03, Example 2 was the same as Example 1.

Example 3

Except for the specific gravity of the hydrophilic solvent 4 being set to 1.13 and the specific gravity of the microbeads 3 being set to 1.03, Example 3 was the same as Example 1.

Example 4

Except for the specific gravity of the hydrophilic solvent 4 being set to 1.3 and the specific gravity of the microbeads 3 being set to 1.03, Example 4 was the same as Example 1.

Comparative Example 2

Except for the specific gravity of the hydrophilic solvent 4 being set to 1 and the specific gravity of the microbeads 3 being set to 1.03, Comparative Example 2 was the same as Example 1.

Comparative Example 3

Except for the specific gravity of the hydrophilic solvent 4 being set to 1.03 and the specific gravity of the microbeads 3 being set to 1.03, Comparative Example 3 was the same as Example 1.

Comparative Example 4

Except for the specific gravity of the hydrophilic solvent 4 being set to 1 and the specific gravity of the microbeads 3 being set to 1.8 (±0.5), Comparative Example 4 was the same as Example 1.

Comparative Example 5

Except for the specific gravity of the hydrophilic solvent 4 being set to 1.03 and the specific gravity of the microbeads 3 being set to 1.8 (±0.5), Comparative Example 5 was the same as Example 1.

Comparative Example 6

Except for the specific gravity of the hydrophilic solvent 4 being set to 1.09 and the specific gravity of the microbeads 3 being set to 1.8 (±0.5), Comparative Example 6 was the same as Example 1.

Comparative Example 7

Except for the specific gravity of the hydrophilic solvent 4 being set to 1.13 and the specific gravity of the microbeads 3 being set to 1.8 (±0.5), Comparative Example 7 was the same as Example 1.

Comparative Example 8

Except for the specific gravity of the hydrophilic solvent 4 being set to 1.3 and the specific gravity of the microbeads 3 being set to 1.8 (±0.5), Comparative Example 8 was the same as Example 1.

<Observation Results>

FIGS. 6(a)-6(d) are photographs illustrating the results of observation of each of the array devices obtained in Examples 2 and 3 and Comparative Examples 2 and 3 using transmitted light microscopy. FIGS. 6(e)-6(h) are explanative diagrams illustrating the results of observation of each of the array devices obtained in Examples 2 and 3 and Comparative Examples 2 and 3 using transmitted light microscopy. FIGS. 6(e)-6(h) illustrate the main part of FIGS. 6(a)-6(d). FIGS. 6(a)-6(h) are illustrated on the same scale. In the following, FIGS. 6(a)-6(h) may be collectively referred to as "FIG. 6".

Figure 6B:
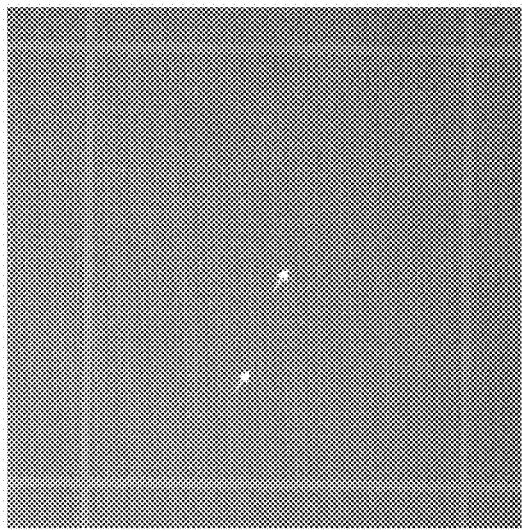
FIGS. 6(a)-6(d) are photographs illustrating the result of observation of an array device and microbeads in Examples 2 and 3 and Comparative Examples 2 and 3 using transmitted light microscopy.
Figure 6D:
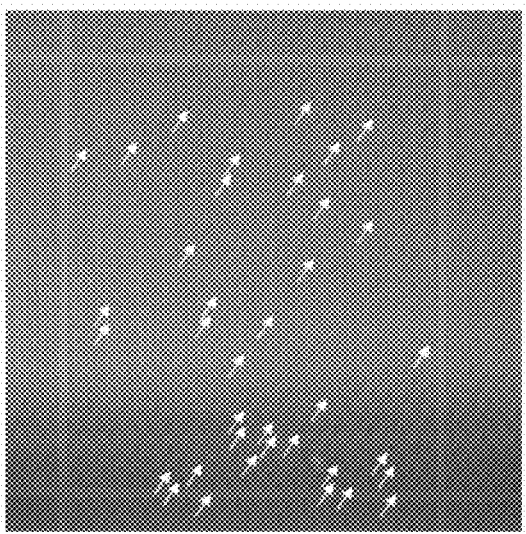
Figure 6A:
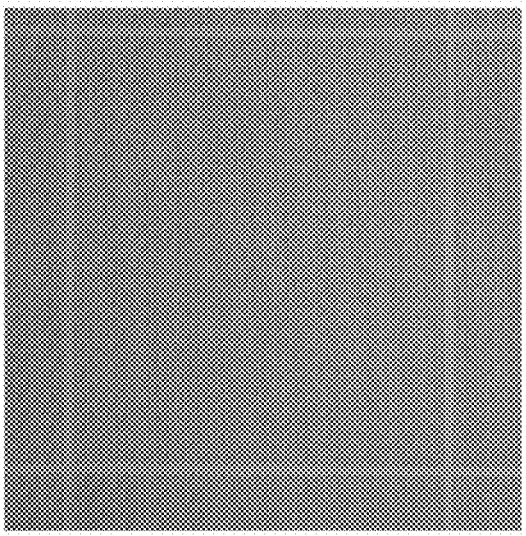
Figure 6C:
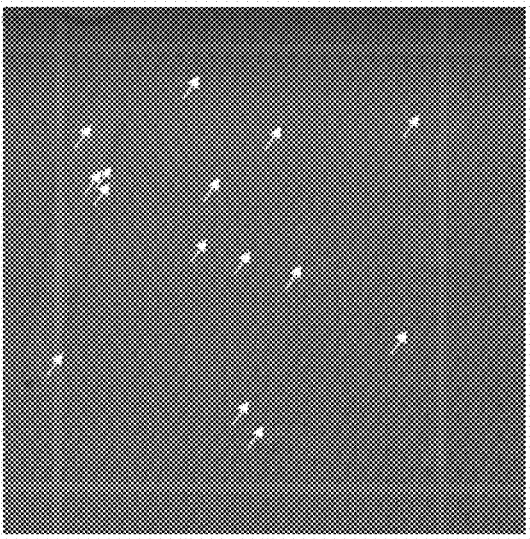
Figure 6F:
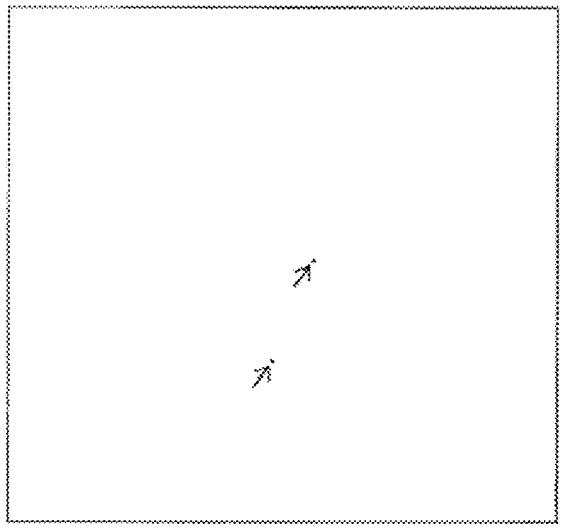
FIGS. 6(e)-6(h) are explanative diagrams illustrating the result of observation of the array device and microbeads in Examples 2 and 3 and Comparative Examples 2 and 3 using transmitted light microscopy.
Figure 6H:
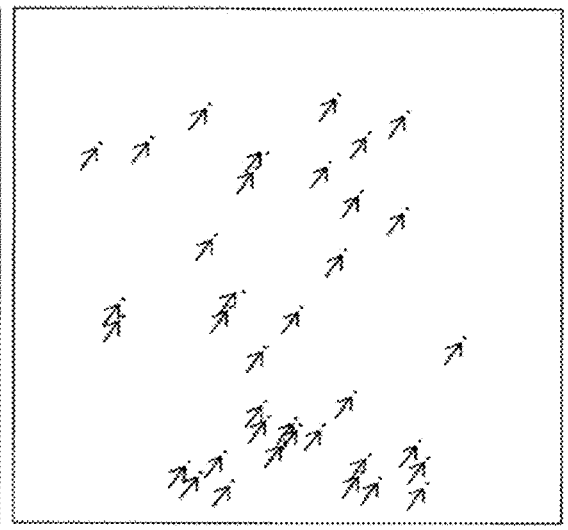
Figure 6E:
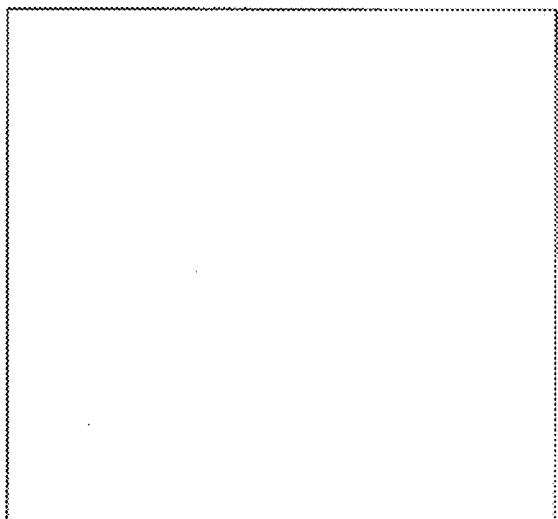
Figure 6G:
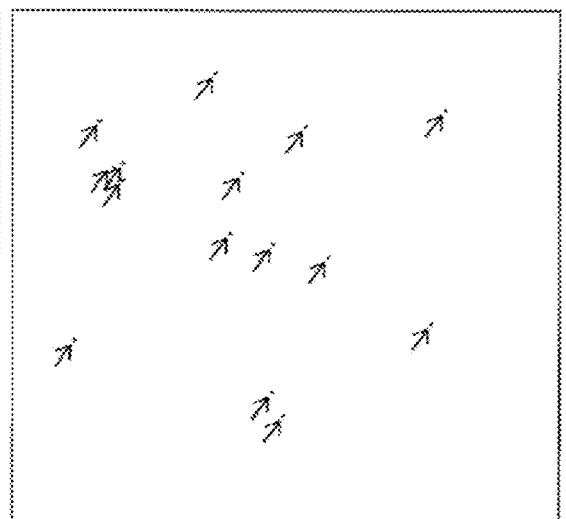

FIGS. 6(a) and 6(e) correspond to Comparative Example 2, FIGS. 6(b) and 6(f) correspond to Comparative Example 3, FIGS. 6(c) and 6(g) correspond to Example 2, and FIGS. 6(d) and 6(h) correspond to Example 3. The observation results of the array device obtained in Example 4 that was observed using transmitted light microscopy are omitted.

FIGS. 7(a)-7(d) are photographs illustrating the results of observation of each of the array devices obtained in Comparative Examples 4 to 7 using transmitted light microscopy. FIGS. 7(e)-7(h) are explanative diagrams illustrating the results of observation of each of the array devices obtained in Comparative Examples 4 to 7 using transmitted light microscopy. FIGS. 7(e)-7(h) illustrates the main part of FIGS. 7(a)-7(d). FIGS. 7(a)-7(h) are illustrated on the same scale. In the following, FIGS. 7(a)-7(h) may be collectively referred to as "FIG. 7".

Figure 7A:
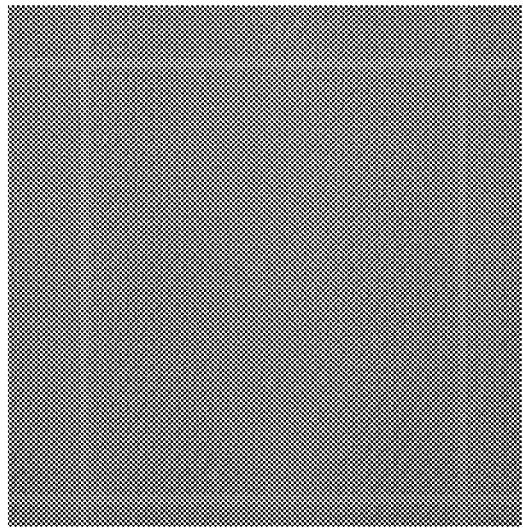
FIGS. 7(a)-7(d) are photographs illustrating the result of observation of an array device and microbeads in Comparative Examples 4 to 7 using transmitted light microscopy.
Figure 7B:
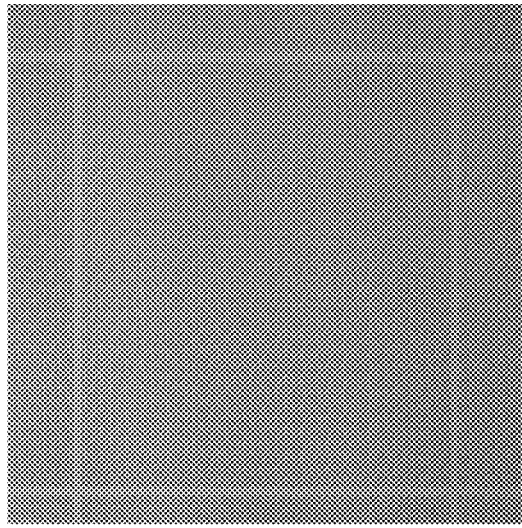
Figure 7C:
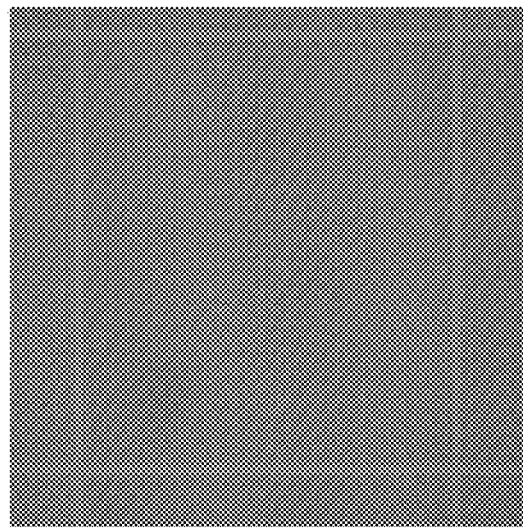
Figure 7D:
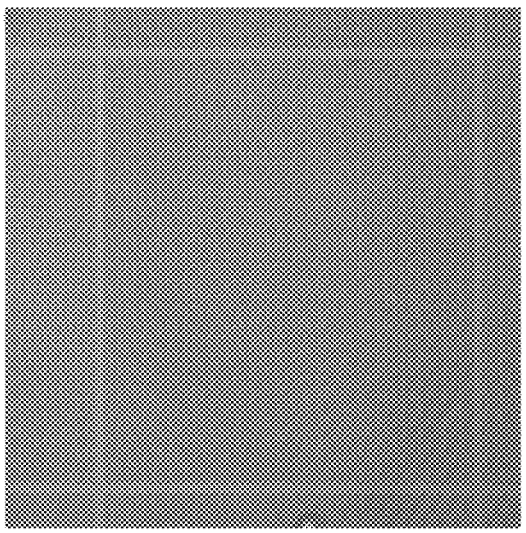
Figure 7F:
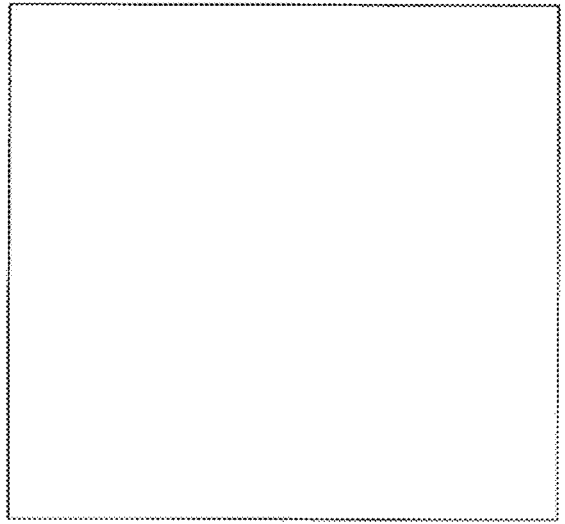
FIGS. 7(e)-7(h) are explanative diagrams illustrating the result of observation of the array device and microbeads in Comparative Examples 4 to 7 using transmitted light microscopy.
Figure 7H:
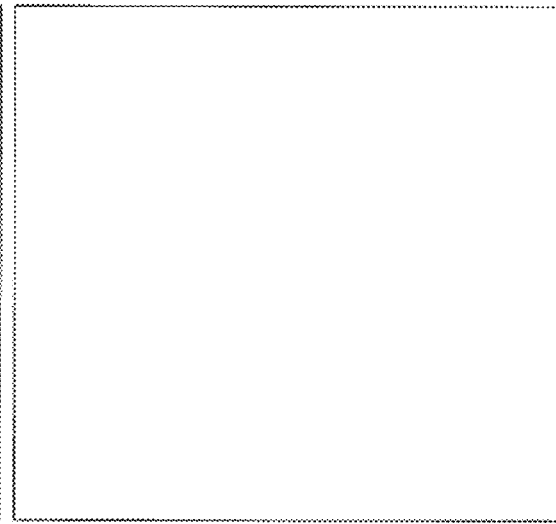
Figure 7E:
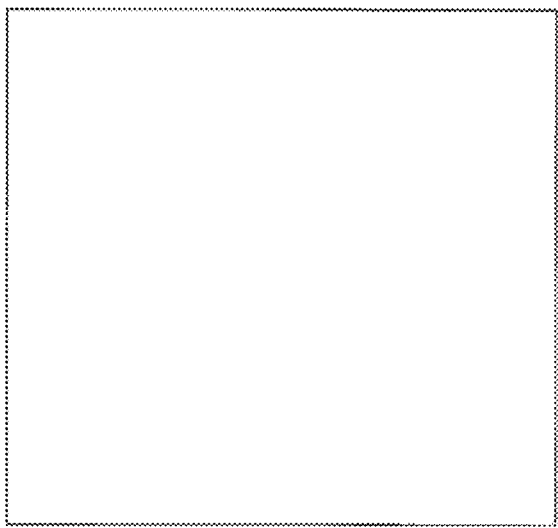
Figure 7G:
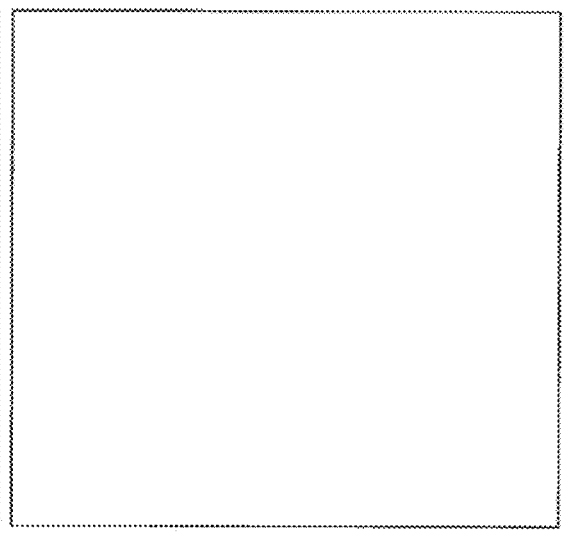

FIGS. 7(a) and 7(e) correspond to Comparative Example 4, FIGS. 7(b) and 7(f) correspond to Comparative Example 5, FIGS. 7(c) and 7(g) correspond to Comparative Example 6, and FIGS. 7(d) and 7(h) correspond to Comparative Example 7. The observation results of the array device obtained in Comparative Example 8 that was observed using transmitted light microscopy are omitted.

In FIG. 6 and FIG. 7, the arrows indicate microwells 2 that contain microbeads 3. That is, the number of microwells 2 that contain microbeads is larger in Example 2 and 3 than in Comparative Examples 2 to 7, or, in other words, it can be seen that more microbeads 3 are contained in the array device. In FIG. 6 and FIG. 7, there are also microwells 2 that contain microbeads 3 other than the portions indicated by the arrows.

In this embodiment, the number of microbeads 3 contained in the microwells 2 of each respective array device obtained in Examples 2 and 3 and Comparative Examples 2 to 7 was measured. The measurement results are given in Table 1. In Table 1, the specific gravity 1.8 (±0.5) of the microbeads 3 is simply written as "1.8".

TABLE 1

| | | Specific Gravity of Beads | | |
|---|---|---|---|---|
| | | 1.03 | | 1.8 |
| Specific Gravity of Aqueous Solution | 1 | Comparative Example 2 | X (0 beads) | Comparative Example 4 X (0 beads) |
| | 1.03 | Comparative Example 3 | Δ (2 beads) | Comparative Example 5 X (0 beads) |
| | 1.09 | Example 2 | ○ (15 beads) | Comparative Example 6 X (0 beads) |
| | 1.13 | Example 3 | ○ (37 beads) | Comparative Example 7 X (0 beads) |
| | 1.3 | Example 4 | ⊚ (3852 beads) | Comparative Example 8 X (0 beads) |

In Example 2, the number of microbeads 3 contained in microwells 2 was 15. In Example 3, the number was 37. In Example 4, the number was 4000. In Comparative Example 2, the number was 0. In Comparative Example 3, the number was 2. In Comparative Examples 4 to 8, the number was 0. In Table 1, as array devices used in the method for detecting a biological substance, unusable devices are indicated by "x, usable devices are indicated by "Δ", suitable devices are indicated by "○", and optimum devices are indicated by "⊚".

From the results above, it was confirmed in more detail that the efficiency of encapsulating microbeads 3 in the microwells 2 becomes higher as the specific gravity of the hydrophilic solvent 4 is made larger than that of the microbeads 3.

Second Embodiment

Figure 8:
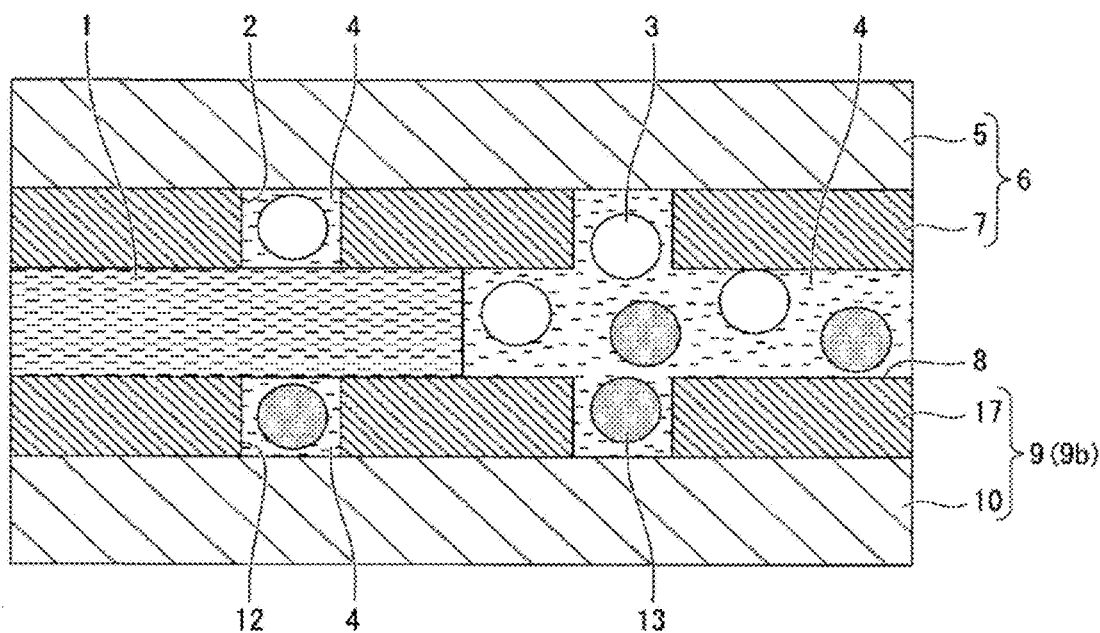
FIG. 8 illustrates in cross-section the configuration of a biomolecule analysis kit employing the method for detecting biological substance according to a second embodiment of the present invention.

FIG. 8 illustrates in cross-section the configuration of a biomolecule analysis kit to which the method for detecting a biological substance according to a second embodiment of the present invention is applied. As illustrated in FIG. 8, the biomolecule analysis kit according to this embodiment includes a substrate portion 6 having a microporous-array layer 7 in which a plurality of microwells 2 as reaction vessels are aligned in an array, and a cover portion 9 (9b) having a microporous-array layer 17 in which a plurality of microwells (second wells) 12 as reaction vessels are aligned in an array, with a flow channel 8 formed between the substrate portion 6 and the cover portion 9b. By introducing the hydrophilic solvent 4 and oily sealant 1 described above into this flow channel 8, a biomolecule analysis kit is formed in which microbeads 3 are contained in the microwells 2, and microbeads (second matter to be contained (second matter), beads) 13 described later are contained in the microwells 12.

In other words, configuration of the biomolecule analysis kit according to this embodiment, except for the cover portion 9b and the microbeads 13, is the same as the configuration of the biomolecule analysis kit described in the first embodiment. Therefore, here, the configuration of the cover portion 9b and the microbeads 13 that differ from the biomolecule analysis kit according to the first embodiment will be described, and description of the other portions will be omitted.

The cover portion 9b includes a cover glass 10 and a microporous-array layer 17 laminated on the cover glass 10 as a reaction field.

For the cover glass 10, the same glass as that used for the cover portion 9a described in the first embodiment can be used. In other words, the same cover glass as that used in the first embodiment can be used. For the microporous-array layer 17, a layer that is the same as the microporous-array layer 7 described in the first embodiment can be used.

The cover portion 9b is disposed on the surface of the substrate portion 6 where the microporous-array layer 7 is formed, and with a space between the cover portion 9b and the substrate portion 6, faces the substrate portion 6 so as to face the open portions of the microporous-array layer 7, that is, the open portions of the microwells 2. More specifically, the cover portion 9b is arranged so that the substrate portion 6 is disposed above the cover portion 9a with a space therebetween. The space between the substrate portion 6 and the cover portion 9b serves as the flow channel 8 through which various fluids flow for detecting a target or the like. In other words, the microwells 2 are positioned above the flow channel 8, and the microwells 12 are positioned below the flow channel 8 so as to face the microwells 2.

The cover portion 9b needs to be observable in the observation direction illustrated in FIG. 8, that is, in a direction toward the microwells 2 from the surface on the opposite side of the cover portion 9b from the flow channel 8. Thus the cover portion 9a preferably is transparent.

In this embodiment, together with the microbeads 3 described in the first embodiment, microbeads 13 are dispersed into the hydrophilic solvent 4 described in the first embodiment.

The material of the microbeads 13 is not limited as long as the microbeads 13 have a smaller specific gravity than the microbeads 3 and the hydrophilic solvent 4, and have a size capable of fitting inside the microwells 12. Preferably, the microbeads 13 are labeled for capturing biomolecules; for example, an antibody or the like is selected to capture protein.

As an example of microbeads 13, magnetic beads can be used. Magnetic beads are magnetic polymer particles containing a magnetic substance and a polymer layer covering the magnetic substance. A magnetic polymer particle may be present as one polymer particle covered by a plurality of magnetic substances. As the substance coating the polymer particles, ferrite particles such as magnetite or the like that is capable of generating minute particles in water are preferable. As a substance other than ferrite, minute particles of various magnetic metals or various magnetic compounds, for example, can be used, and the respective characteristic magnetic properties of these substances can be utilized in various ways. The target substance to be analyzed is then captured by the microbeads 13. The capture method is an antigen-antibody reaction that uses antibody-modified microbeads when the target substance to be analyzed is an antigen protein. When the target substance to be analyzed is DNA, the capture is performed by hybridization using probe-modified microbeads.

As described above, the hydrophilic solvent 4 is such that microbeads 3 and microbeads 13 are respectively dispersed in the hydrophilic solvent 4, and the specific gravity of the hydrophilic solvent 4 is larger than that of the microbeads 3, but smaller than that of the microbeads 13. In other words, the microbeads 3 float in the hydrophilic solvent 4 and the microbeads 13 sink.

Therefore, when hydrophilic solvent 4 is introduced into the flow channel 8, the microbeads 3 are positioned in the upper portion of the flow channel 8, and the microbeads 13 are positioned in the lower portion of the flow channel 8. The microwells 2 are arranged on the top surface of the flow channel 8, and the microwells 12 are arranged on the bottom surface of the flow channel 8, with each of the microwells 2 and microwells 12 open to the flow channel 8 side. Therefore, after a microbead 3 floating in the hydrophilic solvent 4 reaches a position facing a microwell 2, the microbead 3 becomes located in the microwell 2. After a microbead 13 sunk in the hydrophilic solvent 4 reaches a position facing a microwell 12, the microbead 13 becomes located in the microwell 12.

Figure 9:
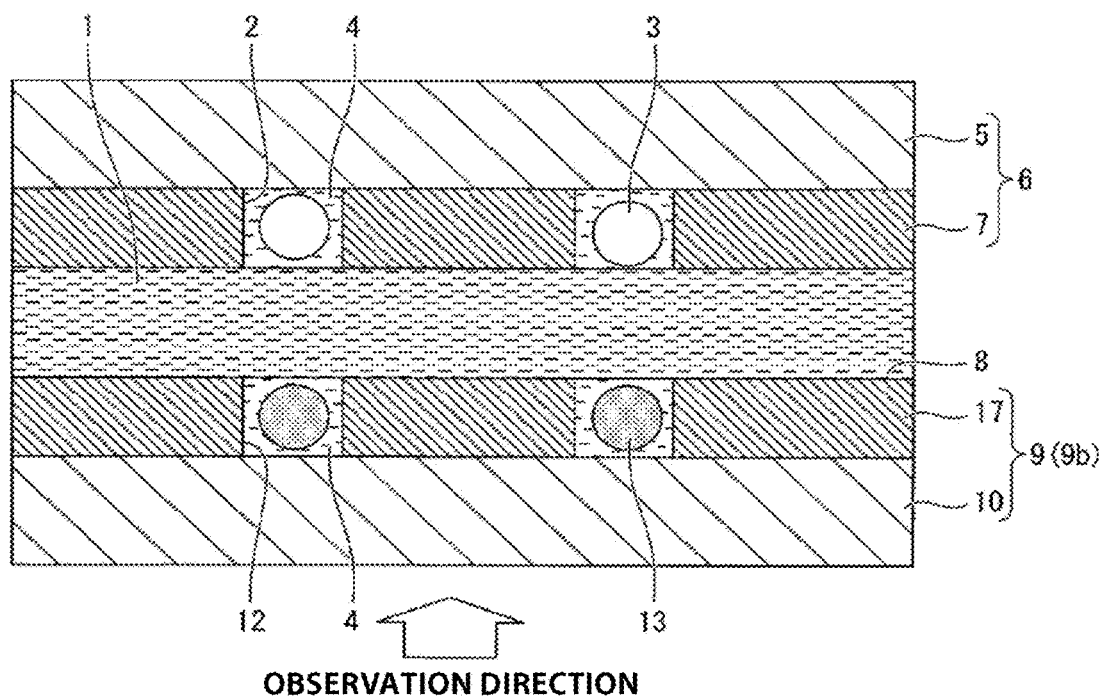
FIG. 9 illustrates in cross-section the configuration of the biomolecule analysis kit employing the method for detecting biological substance according to the second embodiment of the present invention.

After the hydrophilic solvent 4 is introduced into the flow channel 8, the oily sealant 1 is introduced into the flow channel 8. This causes a surplus portion of the hydrophilic solvent 4, that is, the portion not contained inside the microwells 2, to be displaced by the oily sealant 1, so that the flow channel 8 becomes filled with the oily sealant 1. As a result, a biomolecule analysis kit is obtained in which the microbeads 3 are contained inside the microwells 2 and the flow channel 8 is filled with oily sealant 1. FIG. 9 is a cross-sectional view of the biomolecule analysis kit according to this embodiment that is obtained in this way.

Therefore, for example, a signal amplification reaction reagent is contained in the hydrophilic solvent 4 beforehand, a signal amplification reaction is performed inside both the microwells 2 and inside the microwells 12, and signal detection of the microbeads 3 contained inside each of the microwells 2 and the microbeads 13 contained inside each of the microwells 12 is performed. This configuration, for example, allows different analyses to be performed simultaneously while facilitating density detection and the like in each analysis.

The signal amplification reaction described above is the same as the signal amplification reaction described in the first embodiment, so its description is omitted here.

In the biomolecule analysis kit of FIG. 8 and FIG. 9, when viewed from the cover portion 9b side as the observation direction, the microwells 2 in the microporous-array layer 7 overlap with the microwells 12 in the microporous-array layer 17.

When the light emission state is detected using this biomolecule analysis kit, first, for example, the light emission state of the entire area on the substrate portion 6 side is detected by a detection apparatus, the focal point of which is focused on the substrate portion 6 side. Next, the focal point focused on the substrate portion 6 side is focused on the cover portion 9b side, and the light emission state of the entire area on the cover portion 9b side is detected by the detection apparatus. As a result, it is possible to simultaneously perform density detection and the like of different analyses.

Variation of the Second Embodiment

Figure 10:
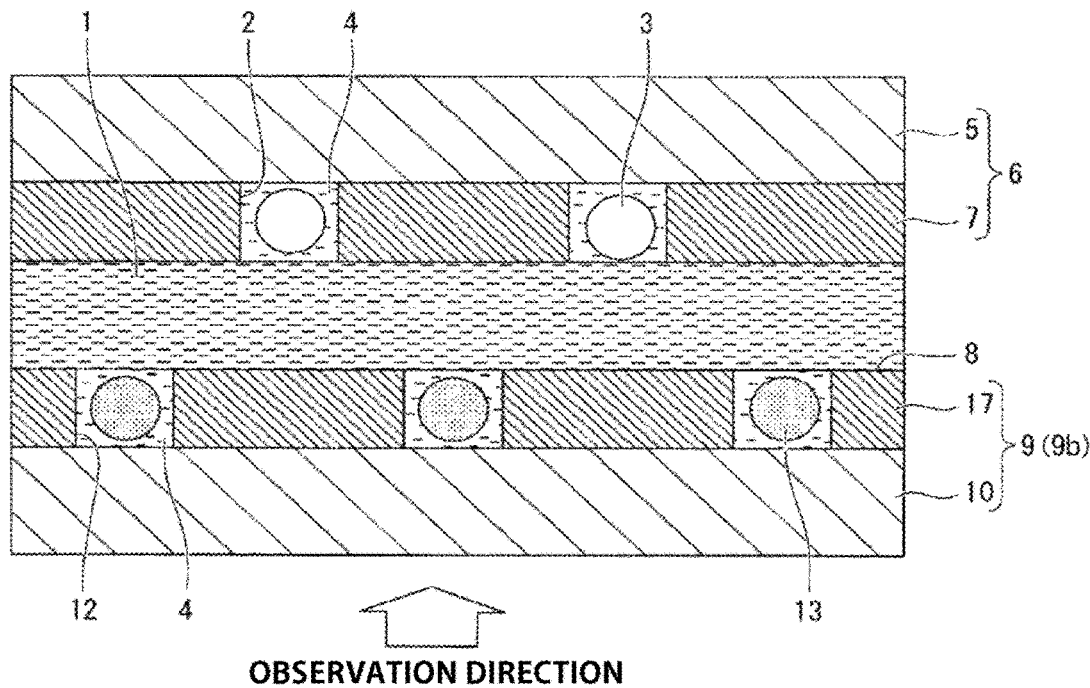
FIG. 10 illustrates in cross-section the configuration of a biomolecule analysis kit employing the method for detecting biological substance according to a variation of the second embodiment of the present invention.

Although in this embodiment the microwells 2 overlap the microwells 12 when viewed from the cover portion 9b side as the observation direction as illustrated in FIG. 8 and FIG. 9, the present invention is not limited to this. For example, as illustrated in FIG. 10, when viewed from the cover portion 9b side as the observation direction, the microwells 2 and the microwells 12 may be arranged so as not to overlap. According to this form, when observed from the cover portion 9b side as the observation direction, the microwells 2 do not overlap the microwells 12, so it is possible to improve both the detection accuracy of the light emission state in the microwells 2 and the detection accuracy of the light emission state in the microwells 12. This point will be described in detail below.

Magnetic beads that can be used as the microbeads 13 are typically black. Therefore, in a biomolecule analysis kit such as illustrated in FIG. 8 and FIG. 9 in which the microwells 2 do not overlap the microwells 12 when viewed from the cover portion 9b side as the observation direction, when magnetic beads are used as the microbeads 13, the detection accuracy of the light emission state in the microwells 12 may decrease. Moreover, the detection accuracy of the light emission state in the microwells 2 may also decrease. This is because the magnetic beads are black, so when viewed from the cover portion 9b side as the observation direction, the magnetic beads become "shadows", and the detection area of the light emission state of the microwells 2 and the microwells 12 becomes narrow.

Second Examples

The effect of the present invention will be described in detail using the following example. The present invention is not limited by this example.

Fluorescent polymer beads having a specific gravity of 1.03, and magnetic beads having a specific gravity of 1.8 (±0.5) were dispersed in a hydrophilic solvent that was adjusted to a specific gravity of 1.13 using Percoll.

Two plates that include microwells were made to face each other, and with a space between them that will become the flow channel 8, were attached together with double-sided tape.

The hydrophilic solvent 4 mixed with the beads was supplied from the supply port of the plates, and after letting the hydrophilic solvent 4 rest for two minutes, oily sealant 1 was supplied.

The beads that were contained in each plate were observed using a microscope in a bright field by transmitted light.

Moreover, the beads that were contained in each plate were observed using fluorescence microscopy As a result, all of the beads contained in the plate that were arranged in the upper portion with microwells that were open facing downwards emitted fluorescent light, so were fluorescent polymer beads having a specific gravity of 1.03. The beads contained in the plate that were arranged in the lower portion with microwells that were open facing upwards did not emit fluorescent light, so were magnetic beads having a specific gravity of 1.8 (±0.5).

Third Embodiment

Figure 11:
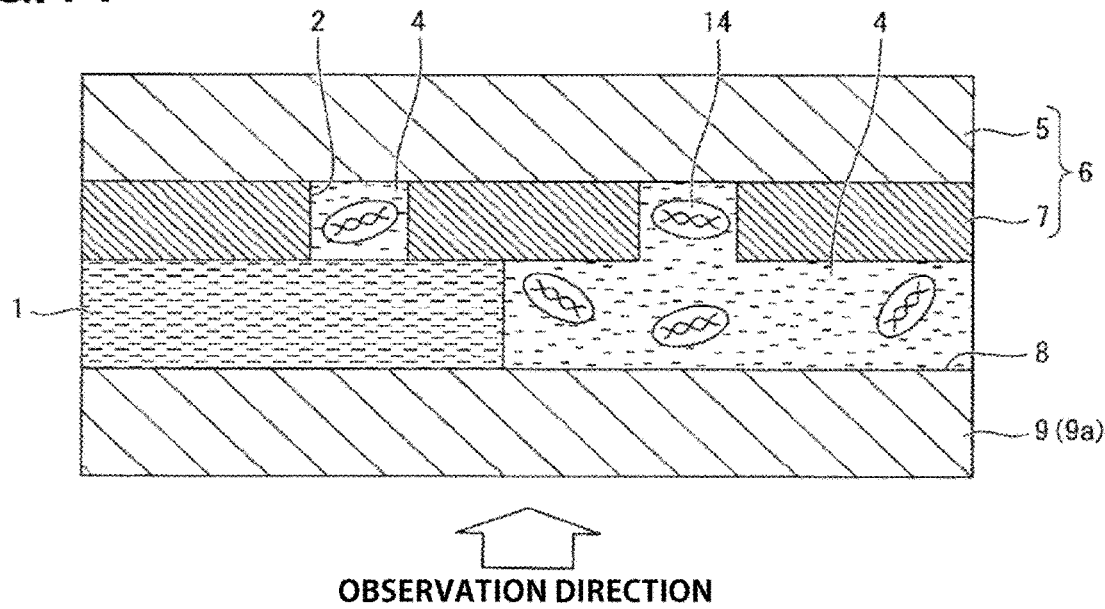
FIG. 11 illustrates in cross-section the configuration of a biomolecule analysis kit employing the method for detecting biological substance according to a third embodiment of the present invention.

FIG. 11 illustrates in cross-section the configuration of a biomolecule analysis kit to which the method for detecting a biological substance according to a third embodiment of the present invention is applied. The biomolecule analysis kit according to this embodiment, as illustrated in FIG. 11, includes a substrate portion 6 that has a microporous-array layer 7 in which a plurality of microwells 2 as reaction vessels are aligned in an array, and a cover portion 9a, and a flow channel 8 is formed between the substrate portion 6 and the cover portion 9a. Then, the hydrophilic solvent 4 and oily sealant 1 described above are introduced into this flow channel 8, to form a biomolecule analysis kit in which a biological substance 14 is contained in the microwells 2.

In other words, except that a biological substance 14 is contained in the microwells 2, the biomolecule analysis kit according to this embodiment is configured in the same way as the biomolecule analysis kit according to the first embodiment. Therefore, here, the biological substance 14 that is the part that differs from the biomolecule analysis kit according to the first embodiment will be described, and description of other parts is omitted.

Examples of the biological substance 14 include, for example, virus particles, bacteria and tissue cells, exosomes, nucleic acid such as DNA, and protein. In the case of these biological substances, the specific gravity is about 1.0 to 1.2, which is small compared with the specific gravity of typical microbeads 3 of 1.0 to 2.5. Therefore, these biological substances 14 can float in various hydrophilic solvents 4.

Therefore, by making the specific gravity of the hydrophilic solvent 4 larger than that of the biological substance, the biological substance 14 is positioned in the upper portion of the flow channel 8 when the hydrophilic solvent 4 is introduced into the flow channel 8. Moreover, microwells 2 are arranged on the top surface of the flow channel 8, and are open to the flow channel 8 side. Therefore, after a biological substance 14 floating in the hydrophilic solvent 4 reaches a position facing a microwell 2, the biological substance 14 becomes located in the microwell 2.

After the hydrophilic solvent 4 is introduced into the flow channel 8, the oily sealant 1 is introduced into the flow channel 8. This causes a surplus portion of the hydrophilic solvent 4, that is, the portion not contained inside the microwells 2, to be displaced by the oily sealant 1, so that the flow channel 8 becomes filled with the oily sealant 1. As a result, a biomolecule analysis kit is obtained in which the biological substance 14 is contained inside the microwells 2 and the flow channel 8 is filled with oily sealant 1.

Therefore, for example, a signal amplification reaction reagent is contained in the hydrophilic solvent 4 beforehand, a signal amplification reaction is performed inside the microwells 2, and signal detection of the biological substance 14 contained inside each of the microwells 2 is performed. This configuration facilitates, for example, density detection and the like.

In a biomolecule analysis kit obtained in this way, the biological substance 14 does not come in contact with the bottom surface of the flow channel 8, that is, the cover portion 9a side. Therefore, when observing from the cover portion 9a side as the observation direction, it is possible to detect the light-emitting state of the biological substance 14 in the entire area on the cover portion 9a side. Therefore, compared with the method of distributing the biological substance 14 into wells formed on the bottom surface side of the flow channel 8, the light-emitting state is detected with higher accuracy, that is, density detection and the like is performed with better accuracy.

The signal amplification reaction described above is the same as the signal amplification reaction described in the first embodiment, so its description is omitted here.

Variation of the Third Embodiment

Although in this embodiment the microwells 2 are only positioned above the flow channel 8 as illustrated in FIG. 11, the present invention is not limited to this. For example, as described in the second embodiment, microwells 12 may also be positioned below the flow channel 8. Such a form, for example, allows different density analyses to be performed simultaneously while facilitating density detection and the like in each analysis.

Effect of Each Embodiment (1) According to one aspect of the present invention, a method for detecting a biological substance includes a distributing process of introducing a hydrophilic solvent 4, in which microbeads 3 are dispersed, into a flow channel 8 to distribute the microbeads 3 into microwells 2 which are recesses capable of containing the microbeads 3, the flow channel 8 being a space between a substrate portion 6 having the microwells 2, with the open side of the microwells 2 facing downwards, and a cover portion 9a disposed on the open side of the microwells 2 so as to face the substrate portion 6, where the hydrophilic solvent 4 has a larger specific gravity than the microbeads 3.

With this configuration, when compared with conventional technology, microbeads 3 are more reliably distributed into microwells 2 formed above the flow channel 8, allowing observation of all of the emitted light.

(2) In a method for detecting biological substance according to one aspect of the present invention, the hydrophilic solvent 4 may contain a signal amplification reaction reagent, a signal amplification reaction may be performed in at least one of the microwells 2 and microwells 12, and signal detection may be performed with the inside of at least one of the microwells 2 and microwells 12 as a target.

With this configuration, when compared with conventional technology, signal detection with the inside of at least one of the microwells 2 and microwells 12 as a target can be performed with higher accuracy.

(3) In a method for detecting biological substance according to one aspect of the present invention, the signal amplification reaction may be an isothermal reaction.

With this configuration, when compared with conventional technology, signal detection with the inside of at least one of the microwells 2 and microwells 12 as a target can be performed with higher accuracy.

(4) In a method for detecting biological substance according to one aspect of the present invention, the isothermal reaction may be an enzyme reaction.

With this configuration, when compared with conventional technology, signal detection with the inside of at least one of the microwells 2 and microwells 12 as a target can be performed with higher accuracy.

(5) In a method for detecting biological substance according to one aspect of the present invention, the enzyme reaction may be an INVADER reaction.

With this configuration, when compared with conventional technology, signal detection with the inside of at least one of the microwells 2 and microwells 12 as a target can be performed with higher accuracy.

(6) In a method for detecting biological substance according to one aspect of the present invention, as the signal, at least any one of fluorescence, light emission, pH change, absorbance change, potential change, and electric current change that correspond to the presence/absence of a biological substance inside the microwells 2 may be detected.

With this configuration, when compared with conventional technology, versatility increases.

(7) In a method for detecting biological substance according to one aspect of the present invention, together with containing any of DNA, RNA, miRNA, mRNA, and protein as the target substance to be analyzed, the hydrophilic solvent 4 may also contain a template nucleic acid as a labeling substance having a specific labeling ability for the target substance to be analyzed, or the labeling substance in a bondable state may be contained in the hydrophilic solvent 4.

With this configuration, when compared with conventional technology, versatility increases.

(8) In a method for detecting biological substance according to one aspect of the present invention, the labeling substance may contain at least one of a DNA chain that is different than the template nucleic acid, an enzyme, a particle, an antibody, and a liposome.

With this configuration, when compared with conventional technology, versatility increases.

(9) The method for detecting biological substance according to one aspect of the present invention, after the distributing process, may also include a process of introducing an oily sealant 1 having a characteristic of not mixing with the hydrophilic solvent 4 into the flow channel 8.

This configuration allows microbeads 3 to be stably distributed into the microwells 2, and all of the emitted light to be observed.

(10) In a method for detecting biological substance according to one aspect of the present invention, the cover portion 9b may include microwells 12 which are recesses capable of containing microbeads 13, with the open side of the of the microwells 12 facing upwards, microbeads 13 are dispersed in the hydrophilic solvent 4, in the distributing process the microbeads 3 are distributed into the microwells 2 and the microbeads 13 are distributed into the microwells 12, and the hydrophilic solvent 4 has a larger specific gravity than the microbeads 3 and has a smaller specific gravity than the microbeads 13.

With this configuration, it is possible to observe all of the light emitted inside the microwells 2 and inside the microwells 12. In other words, it is possible to perform different analyses inside the microwells 2 and inside the microwells 12.

(11) In a method for detecting biological substance according to one aspect of the present invention, the microbeads 13 may be magnetic beads.

This configuration increases the reliability of distributing the microbeads 13 into the microwells 12.

(12) In a method for detecting biological substance according to one aspect of the present invention, the microbeads 3 may be at least one of polymer beads and biological substances.

This configuration increases the reliability of distributing the microbeads 3 into the microwells 2.

Although the present invention has been described with reference to specific embodiments, the present invention is not limited to these descriptions. With reference to the description of the present invention, other embodiments of the present invention, along with various modifications of the disclosed embodiments, will also become apparent to one skilled in the art. Therefore, it is understood that the range of the claims covers these modifications and embodiments included in the scope and spirit of the present invention.

Reference Example

In the following, a method for detecting biological substance other than the method for detecting biological substance according to the present invention will be simply described as a reference example.

Conventionally, it is known that diagnosis of diseases and body constitution is performed by analyzing biomolecules. For example, diagnosis of body constitution by Single Nucleotide Polymorphism (SNP) analysis, determination for administering anticancer agents by somatic cell mutation analysis, countermeasures against infectious diseases by virus protein and DNA analysis, and the like are known.

For example, in the treatment of cancer, it is suggested that by quantifying the number of copies of mutant EGFPs (epidermal growth factor receptors) before and after the administration of EGFR-TKI (tyrosine kinase inhibitor), it is possible to index the therapeutic effect.

Conventionally, quantification was performed using a real-time PCR (Polymerase Chain Reaction); however, it has been learned that the change in the total amount of nucleic acid used in the test affects the quantitativeness, so today digital PCR technology has been developed in which the total amount of nucleic acid does not affect the quantitativeness.

In digital PCR technology, a mixed solution of PCR reaction reagent and nucleic acid is divided into a large number of microdroplets, and PCR amplification is performed on these microdroplets with the nucleic acid among the nucleic acids in the mixture, that is a target of analysis, being a template. Then, a signal such as fluorescent light due to PCR amplification from the microdroplets containing the template nucleic acid is detected, and by finding the ratio of the number of microdroplets in which a signal is detected among the total number of microdroplets, the nucleic acid that is to be detected in the sample is quantified.

For example, Patent Literature 1 and Non-patent Literature 1 describe that by performing an enzyme reaction inside a minute space having a minute volume, it is possible to perform the detection of a biological substance using digital PCR.

Known methods for producing microdroplets for use in digital PCR include a method in which microdroplets are produced by partitioning a mixture of reagent and nucleic acid using a sealant, and a method in which microdroplets are produced by forming a hole in the top of a substrate, and sealing the hole with sealant after a mixture of reagent and nucleic acid is filled into the hole. Patent Literature 2 describes a method of manufacturing an emulsion inside a micro chamber in order to acquire a large amount of experimental data in a short amount of time using a small amount of reagent.

In digital PCR, the mixture of PCR reaction reagent and nucleic acid is diluted so that the number of template nucleic acids present in one microdroplet becomes one or zero. In digital PCR, in order to increase the sensitivity of nucleic acid amplification, and in order to perform nucleic acid amplification on a large number of microdroplets at the same time, preferably the volume of each microdroplet is small.

For example, Non-patent Literature 1 describes a microarray type reaction vessel that is formed so that the volume of each well is 6 nl (nano liters).

Moreover, Non-patent Literature 2 describes a method in which a sample is allowed to flow in a flow channel in a micro array in which plural wells having a depth of 3 μm and diameter of 5 μm are formed in the flow channel, and after the sample is introduced to each of the wells, by displacing the surplus reagent using a sealant, the sample is introduced into each of the wells.

Furthermore, in order to efficiently introduce a biological substance into the microdroplets, microbeads that bond with the biological substance are used, and Patent Literature 3 describes a method of encapsulating the microbeads by using an oil.

The technology of Non-patent Literature 2 allows microbeads to be distributed into wells formed in the bottom surface of a flow channel; however, it sometimes fails to distribute microbeads into microwells provided above the flow channel.

Moreover, with the technology of Non-patent Literature 2, when light emission in the microwells is observed with a microscope, the microbeads are in contact with the bottom surfaces (observation side) of the wells. Therefore, even when the entire surface of the microbeads on the observation side emits light, when observed via the bottom surface of the wells, it is difficult to detect the light emission of the portion in contact with the bottom surfaces of the wells, and it may not be possible to detect all of the light emitted.

Furthermore, when the observation side is above, observation of wells and microbeads on the bottom surfaces must be performed through the flow channel, which is optically disadvantageous.

The present invention has been made in view of this situation. To solve the problem of not being able to detect all of the emitted light, an aspect of the present invention is to provide a method for detecting biological substances, which is capable of distributing beads into wells provided above a flow channel by using a method in which a sample containing beads is allowed to flow along a flow channel of a microarray with many wells formed in the flow channel so that the beads are individually distributed into the wells as a matter to be contained (first matter).

According to one aspect of the present invention, a method for detecting a biological substance includes a distributing process of introducing a solvent, in which a first matter is dispersed, into a flow channel to distribute the first matter into a first well which is a recess capable of containing the first matter, the flow channel being a space between a first substrate having the first well, with the open side of the first well facing downwards, and a second substrate disposed on the open side of the first well so as to face the first substrate, where the solvent has a larger specific gravity than the first matter.

According to one aspect of the present invention, first matters are more reliably distributed into first wells formed above a flow channel, allowing all of the emitted light to be observed.

INDUSTRIAL APPLICABILITY

The embodiments of the present invention can be applied to a biomolecule analysis kit in which beads are contained in a micro reaction vessel for a biochemical reaction in order to detect a biological substance, or can be applied to an array device or the like for quantitative determination of a biological component nucleic acid.

REFERENCE SIGNS LIST

1 Oily sealant
2 Microwell
3 Microbead
4 Hydrophilic solvent
5 Glass substrate
6 Substrate portion
7 Microporous-array layer
8 Flow channel
9 Cover portion 9a Cover portion
9b Cover portion
10 Cover glass
12 Microwell
13 Microbead
14 Biological substance Obviously, numerous modifications and variations of the present invention are possible in light of the above teachings. It is therefore to be understood that within the scope of the appended claims, the invention may be practiced otherwise than as specifically described herein.

What is claimed is:

1. A method of detecting a biological substance, comprising:
    introducing a first substance dispersed in a solvent into a flow channel formed between a first substrate and a second substrate such that the first substance is placed in a first well formed in the first substrate;
    after the introducing of the first substance, introducing into the flow channel a sealant which is immiscible with the solvent; and
    detecting the first substance such that the biological substance is detected,
    wherein the first substance is at least one of the biological substance and a polymer bead comprising the biological substance, the first well is formed such that the first well has an open side which faces downwards and is communicated with the flow channel, and the solvent has a specific gravity larger than a specific gravity of the first substance.

2. The method of claim 1, wherein the solvent includes a signal amplification reaction reagent, and the detecting comprises performing a signal amplification reaction in the first well, and detecting a signal inside the first well.

3. The method of claim 2, wherein the signal amplification reaction is an isothermal reaction.

4. The method of claim 3, wherein the isothermal reaction is an enzyme reaction.

5. The method of claim 4, wherein the enzyme reaction is an assay using a first oligonucleotide which binds to the biological substance, a second oligonucleotide which partially overlaps with the first oligonucleotide and forms an overlapping site when hybridized to the biological substance, and a structure-specific flap endonuclease which cleaves the second oligonucleotide at the overlapping site.

6. The method of claim 2, wherein the detecting of the signal comprises detecting at least one of fluorescence, light emission, pH change, absorbance change, potential change, and electric current change, which correspond to presence or absence of the biological substance inside the first well.

7. The method of claim 1, wherein the biological substance comprises one of DNA, RNA, miRNA, mRNA, and protein, and the solvent further includes a template nucleic acid as a labeling substance having a specific labeling ability for the biological substance or as a labeling substance in a bondable state.

8. The method of claim 7, wherein the labeling substance includes at least one of a DNA chain that is different from the template nucleic acid, an enzyme, a particle, an antibody, and a liposome.

9. The method of claim 1, wherein the first substance is the polymer bead comprising the biological substance.

10. A method of detecting a biological substance, comprising:
    introducing a first substance dispersed in a solvent into a flow channel formed between a first substrate and a second substrate such that the first substance is placed in a first well formed in the first substrate;
    introducing a second substance comprising a magnetic bead and dispersed in the solvent into the flow channel such that the second substance is placed in a second well formed in the second substrate; and
    detecting the first substance such that the biological substance is detected,
    wherein the first substance is at least one of the biological substance and a polymer bead comprising the biological substance, the first well is formed such that the first well has an open side which faces downwards and is communicated with the flow channel, and the solvent has a specific gravity larger than a specific gravity of the first substance and smaller than a specific gravity of the second substance, and the second well is formed in the second substrate such that the second well has an open side which faces upwards and is communicated with the flow channel.

11. The method of claim 10, wherein the first substance is the polymer bead comprising the biological substance.

12. The method of claim 10 wherein the introducing of the second substance is at the same time as the introducing of the first substance.

13. The method of claim 10, wherein the solvent includes a signal amplification reaction reagent, and the detecting comprises performing a signal amplification reaction in the first well, and detecting a signal inside the first well.

14. The method of claim 13, wherein the signal amplification reaction is an isothermal reaction.

15. The method of claim 14, wherein the isothermal reaction is an enzyme reaction.

16. The method of claim 15, wherein the enzyme reaction is an assay using a first oligonucleotide which binds to the biological substance, a second oligonucleotide which partially overlaps with the first oligonucleotide and forms an overlapping site when hybridized to the biological substance, and a structure-specific flap endonuclease which cleaves the second oligonucleotide at the overlapping site.

17. The method of claim 13, wherein the detecting of the signal comprises detecting at least one of fluorescence, light emission, pH change, absorbance change, potential change, and electric current change, which correspond to presence or absence of the biological substance inside the first well.

18. The method of claim 10, wherein the biological substance comprises one of DNA, RNA, miRNA, mRNA, and protein, and the solvent further includes a template nucleic acid as a labeling substance having a specific labeling ability for the biological substance or as a labeling substance in a bondable state.

19. The method of claim 18, wherein the labeling substance includes at least one of a DNA chain that is different from the template nucleic acid, an enzyme, a particle, an antibody, and a liposome.

20. The method of claim 10, further comprising:
    after the introducing of the first substance, introducing into the flow channel a sealant which is immiscible with the solvent.

* * * * *